(12) United States Patent
Blocher et al.

(10) Patent No.: US 8,926,549 B2
(45) Date of Patent: Jan. 6, 2015

(54) HANDLE FOR A MEDICAL INSTRUMENT

(75) Inventors: Martin Blocher, Tuttlingen (DE);
Dominik Volkmer, Fridingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1079 days.

(21) Appl. No.: 12/432,362

(22) Filed: Apr. 29, 2009

(65) Prior Publication Data
US 2009/0270842 A1 Oct. 29, 2009

(30) Foreign Application Priority Data
Apr. 29, 2008 (DE) .................... 20 2008 005 899 U

(51) Int. Cl.
*A61M 1/00* (2006.01)
*A61M 25/16* (2006.01)
*A61M 25/18* (2006.01)
*A61M 39/00* (2006.01)
*A61M 39/10* (2006.01)
*A61M 39/12* (2006.01)

(52) U.S. Cl.
CPC .............. *A61M 39/12* (2013.01); *A61M 1/0043* (2013.01); *A61M 1/0064* (2013.01); *A61M 1/0045* (2013.01); *A61M 39/1011* (2013.01)
USPC .............. 604/27; 604/533; 604/534; 604/535

(58) Field of Classification Search
USPC ................. 604/533, 34, 35, 19, 27, 534, 535; 433/126
See application file for complete search history.

(56) References Cited

U.S. PATENT DOCUMENTS

| 4,723,948 A |   | 2/1988  | Clark et al.     |        |
|-------------|---|---------|------------------|--------|
| 5,147,292 A | * | 9/1992  | Kullas et al.    | 604/34 |
| 5,792,098 A | * | 8/1998  | Felix et al.     | 604/27 |
| 5,989,211 A | * | 11/1999 | Schaumann et al. | 604/27 |

FOREIGN PATENT DOCUMENTS

| DE | 4321110 A1    | 1/1994  |
| DE | 19647816 C2   | 5/2003  |
| WO | 2009000439 A1 | 12/2008 |

OTHER PUBLICATIONS

German Search Report; Application No. 20 2008 005 899.6; Jul. 1, 2008; 4 pages.
European Search Report; EP 09 00 4828; Jul. 24, 2009; 6 pages.

* cited by examiner

*Primary Examiner* — Theodore Stigell
*Assistant Examiner* — Shefali Patel
(74) *Attorney, Agent, or Firm* — St. Onge Steward Johnston & Reens LLC

(57) ABSTRACT

A handle for a medical instrument having a handle housing that can be closed by a cover and having at least one drainage or irrigation hose in the handle housing that can be connected to a hose connection support. To create a handle that is of a simple construction and ensures a reliable fluid-proof insulated connection of the at least one hose and the hose connection support while protecting a material of the at least one hose, it is proposed that each drainage or irrigation hose should be connectable by an adaptor to the hose connection support and that the adaptor upon closing the handle housing can be pressed against the hose connection support by a stop positioned on the cover or on a base portion of the handle housing.

12 Claims, 3 Drawing Sheets

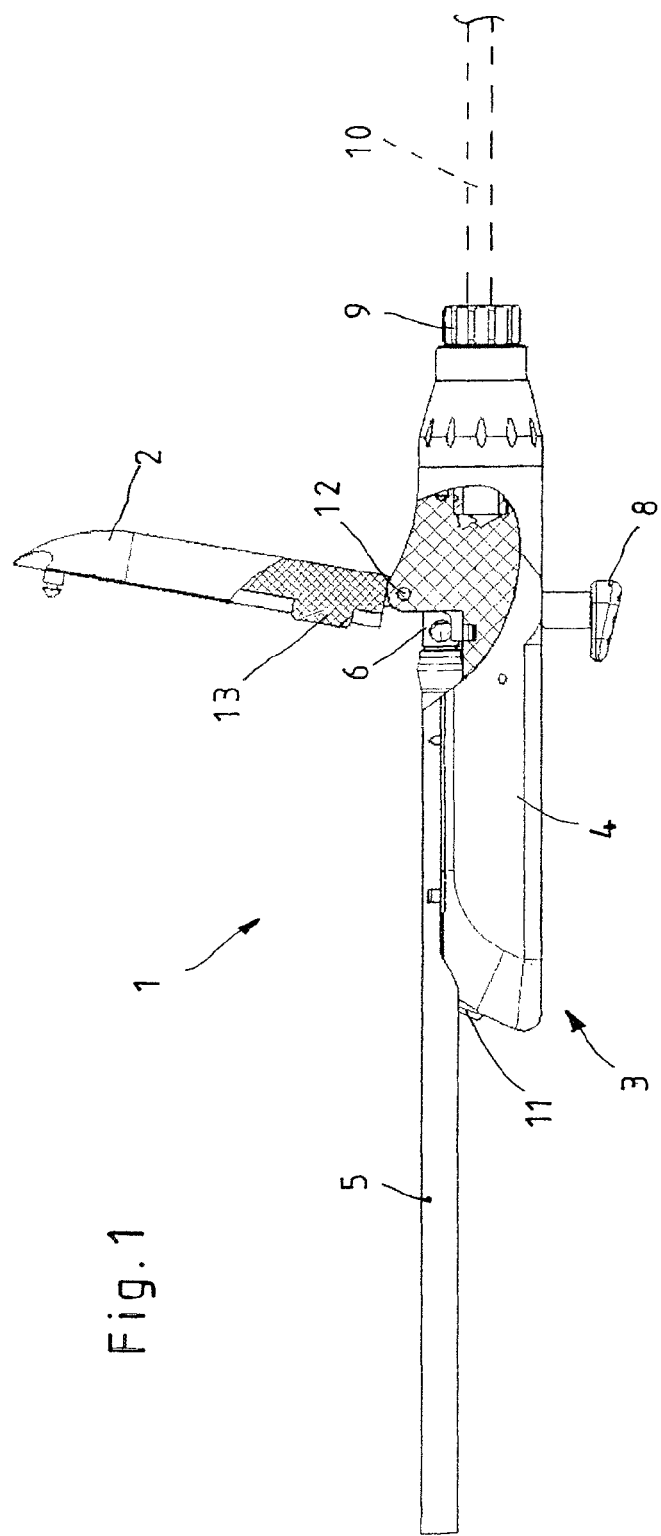
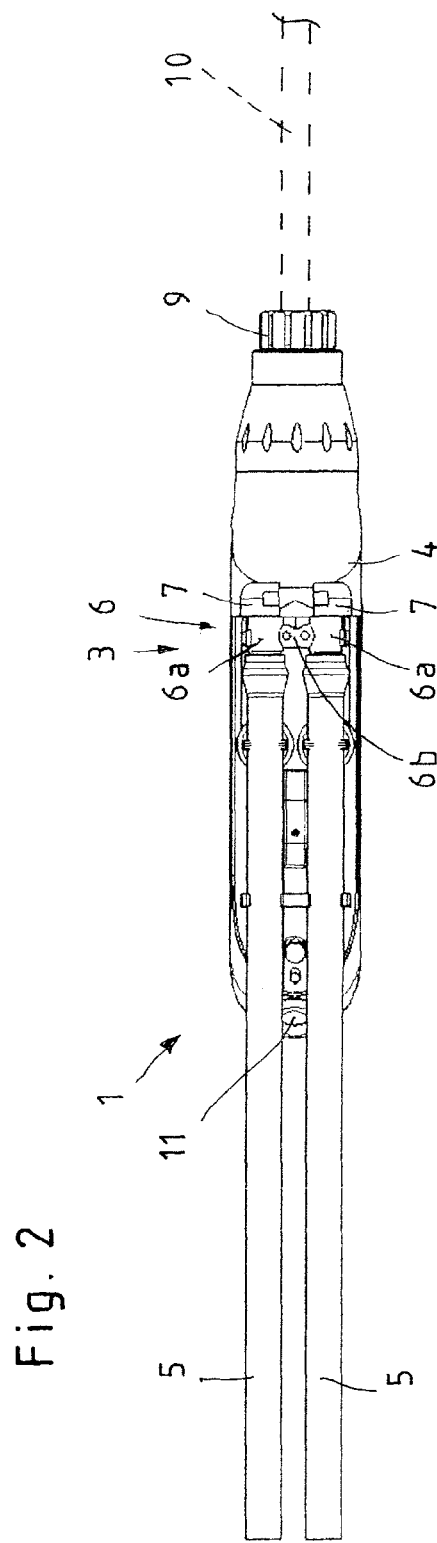
Fig. 1
Fig. 2

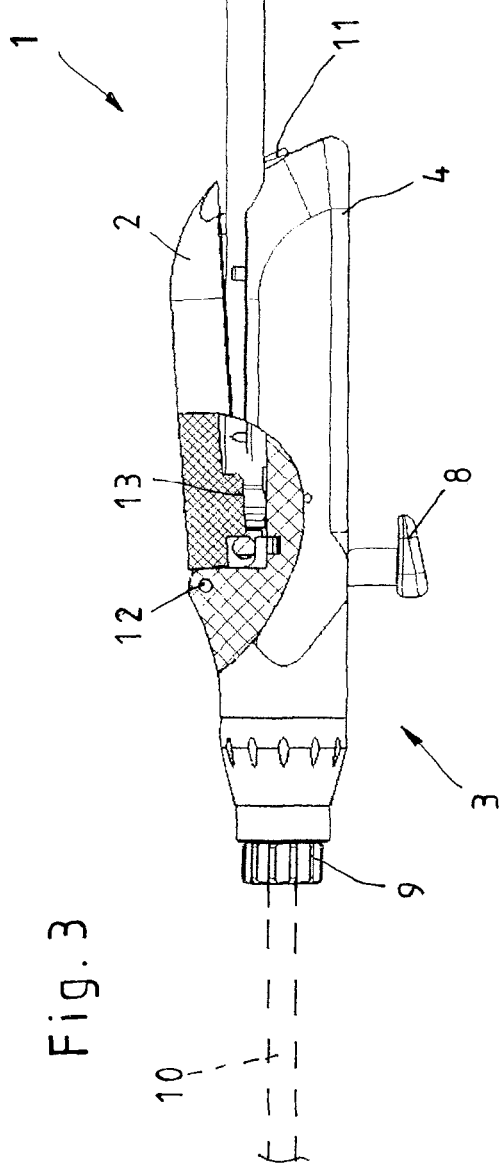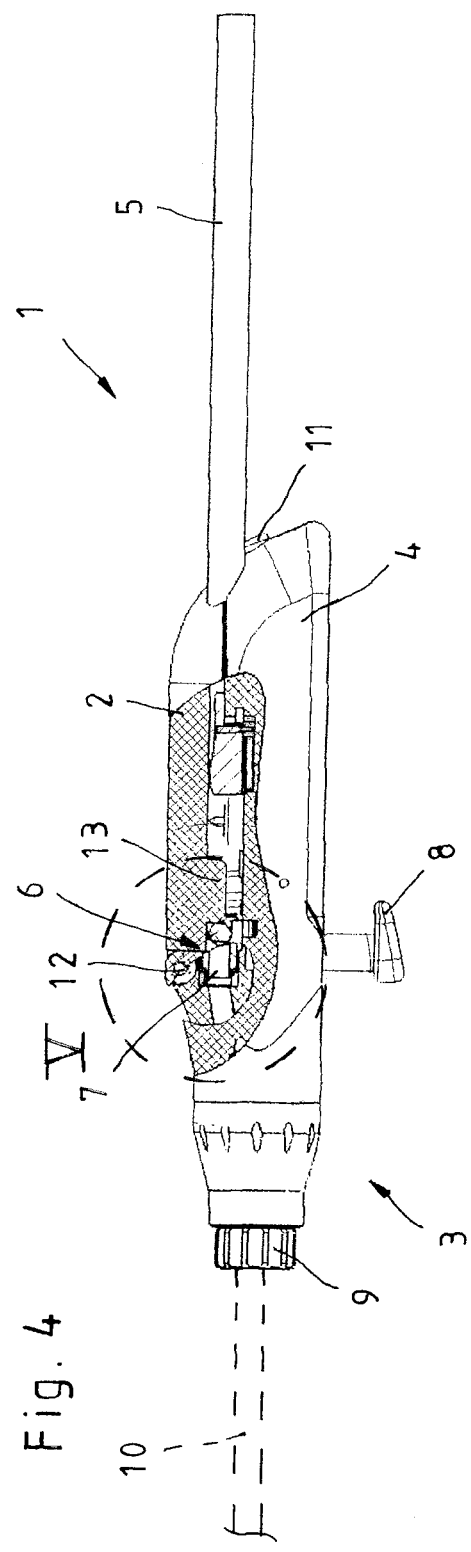

HANDLE FOR A MEDICAL INSTRUMENT

CROSS-REFERENCE TO RELATED APPLICATIONS

The present application claims priority of German patent application No. 20 2008 005 899.6 filed on Apr. 29, 2008, the content of which is incorporated herein by reference.

FIELD OF THE INVENTION

The invention relates to a handle for a medical instrument having a handle housing that can be closed by means of a cover and having at least one drainage or irrigation hose that can be connected to a hose connection support.

BACKGROUND OF THE INVENTION

In order to ensure the operator a good view of the surgical area, in particular during endoscopic procedures, it is often necessary to clean the surgical area with an irrigating fluid and to drain the surgical area of irrigating fluid and blood run-off. For this purpose, corresponding medical instruments have been equipped with drainage and/or irrigation hoses, which can be operated by means of the handle of the particular instrument.

Medical instruments known in the art have the problem that they are difficult to clean in the area of the handle that has the hose connection support and, in addition, cannot ensure adequate liquid-tight insulation against leakage.

A generic handle is disclosed, for instance, in patent DE 196 47 816 C2. With this familiar medical instrument from the art, two hoses that can be secured to the connection supports are positioned inside the handle. Semicircular pressure surfaces with circle-segment-shaped ridges are formed to match the rotatable housing portion of the handle and, with the handle in closed position, partly surround the hoses in such a way that the hose material is radially pressed against the connection supports. Because of the effect of pressure surfaces on the hose material, said material is clinched in the area of the hose connection supports.

Consequently it is the object of the invention to create a handle of the aforementioned type that is of simple construction and secures a reliable liquid-proof-insulated connection of the hose and the hose connection supports while also protecting the hose material.

SUMMARY OF THE INVENTION

The invention fulfills the object in that every drainage and/or irrigation hose can be connected by an adaptor to the related hose connection support and that, on closing the handle housing, the adaptor can be pressed against the hose connection support by means of a stop positioned on the cover and/or on the base portion of the handle housing.

Because of the inventive use of an adaptor for connecting each and every drainage and/or irrigation hose to its related hose connection support, the hose ends are preserved because the actual contact with the hose connection supports is provided by the interposed adaptor. The configuration of a stop on the cover and/or on the handle housing, which is in contact with the adaptor upon closing the handle housing, ensures that during every closing of the handle housing the adaptor is automatically pressed against the related hose connection support by means of the stop while being insulated and with a uniform pressure maintained.

According to a preferred embodiment of the invention it is proposed that the stop should be configured as a stud formed to match the cover and pointing inward. The positioning of the stop on the housing cover constitutes an embodiment that is especially simple to manufacture and that can be operated without problems.

As an alternative to the positioning of the stop on the cover of the handle it is also possible of course to place the stop on the lower portion of the handle housing in such a way that the stop is pressed against the adaptor while the cover is being closed.

It is proposed with a first practical embodiment of the invention that the adaptor should be configured in H-shape for connecting two hoses to two hose connection supports.

In a second inventive embodiment it is proposed that the adaptor should be of U-shaped configuration for connecting two hoses to two hose connection supports.

Finally, it is proposed with the invention that to improve the fluid-proof insulated mounting of the adaptor on the related hose connection support, at least one insulating element, in particular an O-ring insulation, should be secured on the adaptor and/or on the hose connection support. The insulation element is shaped for insulating effect by pressing the adaptor against the hose connection support.

In addition it is proposed with the invention that for insulation with respect to the hose connection support the adaptor should consist of an insulation material, in particular silicon.

Further characteristics and advantages of the invention can be seen from the appended illustration, which depicts an embodiment of an inventive handle for a medical instrument in merely exemplary form, without restricting the invention to this embodiment.

BRIEF DESCRIPTION OF THE DRAWINGS

FIG. 1 shows a partly cut-out side view of an inventive handle with the cover opened.

FIG. 2 shows an overhead view of the handle from FIG. 1, but without cover.

FIG. 3 shows a side view as in FIG. 1 with a partly closed cover.

FIG. 4 shows a side view as in FIG. 3 with closed cover.

DETAILED DESCRIPTION OF THE INVENTION

Figure 5:
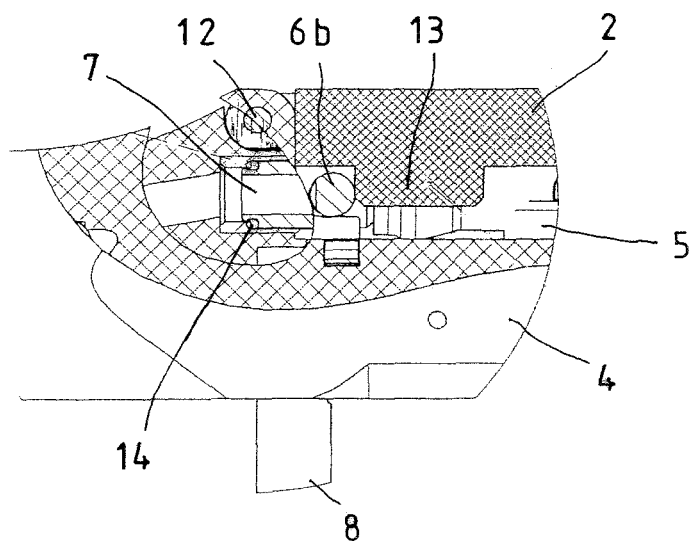
FIG. 5 shows an enlarged view of detail V of FIG. 4.

FIGS. 1 through 4 shows a handle 1 for a medical instrument having a handle housing 3 that can be closed by means of a cover 2, where the handle housing 3 consists essentially of a base portion 4 and the cover 2.

In the illustrated embodiment of the handle 1, two drainage and/or irrigation hoses 5 in the handle housing 3 can be connected by an adaptor 6 to two hose connection supports 7, but it is also possible to execute handles 1 having only one drainage and/or irrigation hose 5 or having more than two hoses 5. In any case, however, the distal end of each drainage and/or irrigation hose 5 can be secured onto an adaptor 6, which in turn can be connected to the related hose connection supports 7.

Use of the adaptor 6 for securing a drainage and/or irrigation hose 5 to the related hose connection support 7 has the advantage that the draining and/or irrigation hose 5 is connected to the hose connection support 7 indirectly, that is, by means of the interposed adaptor 6, so that the hose material can be protected in making the connection and does not require any occasional stretching and clinching of the hose material in pushing it up and pressing it onto the hose connection supports 7.

By means of the draining and irrigation housing 5, irrigation liquid is conducted to the surgical area and is drained out of the surgical area again in order to ensure the operator a good view of the surgical area.

To modulate the drainage and/or irrigation capacity that is to be provided by the hoses 5, the handle 1 also comprises two keys 8 that are positioned on the base portion 4 and by which the passage of liquid through the hoses 5 can be throttled. Only one key 8 can be seen in each of FIGS. 1, 2, and 4 because the keys in these side views are positioned directly behind one another. The number of keys 8, however, corresponds as a rule to the number of the hoses 5 positioned in the handle 1.

On its distal end the handle 1 comprises a coupling element 9 in the form of a clamping screw device, by means of which, for instance, an instrument shaft 10 (indicated with broke lines) can be secured on the handle 1.

As can be seen in FIG. 2, the adaptor 6 in the embodiment illustrated here for coupling two hoses 5 with two hose connection supports 7 is configured in an H-shape in such a way that the hoses 5 are pushed onto the proximal-side free ends of the longitudinal sides 6a of the H-shaped adaptor 6, whereas the distal-side free ends of the longitudinal sides 6a of the H-shaped adaptor 6 serve for coupling with the two hose connection supports 7.

Figure 6:
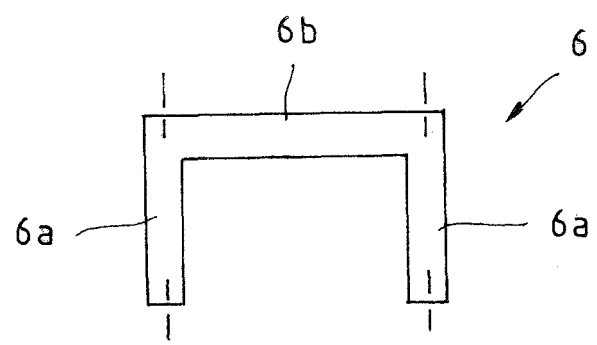
FIG. 6 shows an enlarged schematic view of a second embodiment of an adaptor.

In the alternative embodiment shown in FIG. 6, the adaptor 5 is of U-shaped configuration in such a way that the hoses 5 are pushed onto the proximal-side free ends of the longitudinal sides 6a of the U-shaped adaptor 6, whereas on the distal side a connection stud 6b that connects the two longitudinal sides 6a of the U-shaped adaptor 6 with one another serves for coupling with the two hose connection supports 7.

The hoses 5 are connected to the hose connection supports 7 of the handle 1 as follows:

In the first step of the operation a blocking mechanism 11 is actuated on the handle housing 3 in order to unlock the cover 2 from its catch-lock connection on the base portion 4. Thereafter the cover 2 can be rotated into the opened position around an axis of rotation 12 by about 90 degrees with respect to the base portion 4, as said position is shown in FIG. 1.

Hereafter the two hoses 5 are pushed from the same side as far as possible onto the free ends of the longitudinal side 6a of the H- or U-shaped adaptor 6. This hose set, connected in such a manner with the adaptor 6, is now inserted into the base portion 4 of the handle 1 in such a way that it does not come into contact with the free ends of the longitudinal sides 6a of the H-shaped adaptor 6 on the hose connection supports 7, which free ends are now connected with hoses 5, as can be seen from the overhead view of FIG. 2. To connect the hoses 5 in accordance with their function as drainage or irrigation hoses 5 on the correct hose connection supports 7, at least one hose 5 comprises a color or sign coding system that is here located, accordingly, on the related hose connection supports 7.

For liquid-proof insulation of the adaptor 6 onto the hose connection supports 7, it is decisive that the adaptor 6 is pushed sufficiently deeply into the hose connection supports 7.

For this purpose, on the inside of the cover 2 that faces the interior of the handle housing 3, a stop 13 is configured which in the illustrated embodiment, as can be recognized in FIGS. 1, 3, 4, and 5, is configured as a narrow stud.

This stop 13 is positioned on the inside of the cover 2 in such a way that upon closing the cover, as shown in FIGS. 3, 4, and 5, said stop comes into contact with the connecting stud that connects the two longitudinal sides 6a of the H- or U-shaped adaptor 6 with one another and thus presses the adaptor 6 in the distal direction against the hose connection supports 7.

The stop 13 thus has the effect that upon closing the cover 2 the adaptor 6 attached with the hoses 5 is automatically pressed against the hose connection supports 7 in fluid-proof insulation. As can be seen from FIGS. 4 and 5, when the cover 2 is closed the stop 13 is in contact with the connecting stud 6b of the adaptor 6 and thus ensures that the adaptor 6 cannot be moved out of its fluid-proof insulation on the hose connection supports 7 even with pulling pressure in the proximal direction.

To improve still further the fluid-proof insulation of the adaptor 6 on the hose connection supports 7, insulating elements 14, in particular in the form of O-ring insulations, are secured on the free ends of the longitudinal sides 6a of the H-shaped adaptor 6, to insulate with respect to the hose connection supports 7, said insulating elements being shaped for insulation when the adaptor 6 is pressed against the hose connection supports 7.

It is likewise possible to position insulating elements 14 on sides of the hose connection supports 7 in order to ensure fluid-proof insulation of the adaptor 6 on the hose connection supports 7.

As an alternative to the illustrated embodiment it is also possible, of course, to position the stop 13 on the base portion 4 in such a way that said stop is in contact with the adaptor 6 on closing the cover 2 and presses the adaptor 6 against the hose connection supports 7 with fluid-proof insulation.

A handle of this type of configuration is characterized in that it is of simple construction, easy to install and clean, and, every time the cover 2 of the handle housing 3 is closed, it automatically ensures that the hoses 5 are connected to the hose connection supports 7 by the adaptor 6 to provide fluid-proof insulation.

What is claimed is:

1. A handle for a medical instrument having a handle housing that is closeable by means of a cover and having at least one drainage or irrigation hose in the handle housing for being connected to a hose connection support, wherein each drainage or irrigation hose being connectable to the hose connection support by means of one adaptor and, on closing the handle housing, the one adaptor is pressed against the hose connection support by means of a stop positioned on the cover or on a base portion of the handle housing and acting directly on the one adaptor, wherein the one adaptor is configured as a single adaptor adapted to connect two hoses to two hose connection supports.

2. The handle according to claim 1, wherein the stop is configured as a stud that is formed to match the cover and point inward.

3. The handle according to claim 2, wherein the adaptor is of an H-shaped configuration for connecting the two hoses to the two hose connection supports.

4. The handle according to claim 2, wherein the adaptor is of a U-shaped configuration for connecting the two hoses to the two hose connection supports.

5. The handle according to claim 1, wherein the adaptor is of an H-shaped configuration.

6. The handle according to claim 1, wherein the adaptor is of a U-shaped configuration.

7. The handle according to claim 1, wherein at least one insulation element can be secured on the adaptor for insulating with respect to the hose connection support.

8. The handle according to claim 7, wherein at least one O-ring-insulation can be secured on the adaptor for insulating with respect to the hose connection support.

9. The handle according to claim 1, wherein at least one insulation element can be secured on the hose connection support for insulating with respect to the adaptor.

10. The handle according to claim 9, wherein at least one O-ring-insulation can be secured on the hose connection support for insulating with respect to the adaptor.

11. The handle according to claim 1, wherein the adaptor consists of an insulation material for insulating with respect to the hose connection support.

12. The handle according to claim 11, wherein the adaptor consists of silicon for insulating with respect to the hose connection support.

* * * * *